United States Patent [19]

Solladie et al.

[11] Patent Number: 5,296,611
[45] Date of Patent: Mar. 22, 1994

[54] PROPENALS SUBSTITUTED WITH A DITHIANE RING AND PROCESSES FOR THE PREPARATION OF THESE PROPENALS

[75] Inventors: Guy Solladie, Strasbourg; Valerie Berl, Mulhouse; Jean Maignan, Tremblay-les-Gonesse, all of France

[73] Assignee: L'Oreal, Paris, France

[21] Appl. No.: 897,778

[22] Filed: Jun. 12, 1992

[30] Foreign Application Priority Data

Jun. 14, 1991 [FR] France .................. 91 07293

[51] Int. Cl.$^5$ .......................... C07D 339/08
[52] U.S. Cl. .......................... 549/21; 549/22
[58] Field of Search .................. 549/21, 22

[56] References Cited

PUBLICATIONS

Solladié et al, Synett, Nov. 1991, pp. 795 & 796.
Sato et al: "Preparation of chiral C5-building blocks for terpene synthesis by bakers' yeast reduction of sulfur-functionalized prenyl derivatives", Tetrahedron Letters, vol. 29, No. 18, (1988), pp. 2197–2200.
Rustemeier et al: "(E)-3-(1,3-Dithian-2-yl) acroleine als geschotzte Fumardialdehyde durch Oxopropenylierung des 1,3-Dithians", Chemische Berichte, vol. 115, No. 12 (1982), pp. 3898–3903.
Greene, "Protective books in Organic Synthesis" (1981) pp. 133–140.
G. Solladie et al, Chemical Abstracts 116: 83604n, p. 813, (1992).
G. Solladie et al., Tetrahedron Letters, 32 (44), pp. 6329–6332 (1991).
F. Carey et al., "Advanced Organic Chemistry," 2nd ed, 205–206 (1983) Plenum Press, New York.

Primary Examiner—Richard L. Raymond
Attorney, Agent, or Firm—Cushman, Darby & Cushman

[57] ABSTRACT

Propenals of formula:

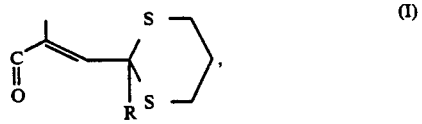

(I)

in which formula R is H or a $C_1$–$C_4$ thioalkyl radical, the dithiane ring being at the cis position in relation to the aldehyde function when R is H and at the trans position when R is a thioalkyl radical. The invention also relates to two processes for the preparation of these propenals.

4 Claims, No Drawings

PROPENALS SUBSTITUTED WITH A DITHIANE RING AND PROCESSES FOR THE PREPARATION OF THESE PROPENALS

The present invention relates to propenals substituted with a dithiane ring at the chain end and having a cis- or trans-stereospecific structure, and to processes for preparing these propenals which make it possible to obtain them with a high stereospecificity.

The present invention thus has as first subject the propenals of general formula (I):

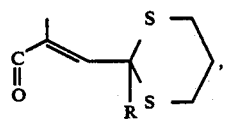
(I)

in which formula R is hydrogen or a $C_1$-$C_4$ thioalkyl radical, the dithiane ring being at the cis position with respect to the aldehyde function when R is H, and at the trans position when R is a thioalkyl radical.

In the present text and by convention, the trans position of the dithiane ring is represented by putting the axis of symmetry of this ring obliquely upwards and the cis position by orienting the said axis downwards. When this axis is represented horizontally, the formula denotes without distinction the cis-stereospecific form or the trans-stereospecific form.

A subject of the present invention is more particularly the cis-propenal of formula (Ia):

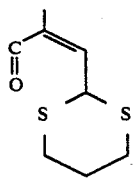
(Ia)

and the trans-propenal of formula (Ib):

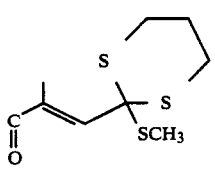
(Ib)

These compounds are starting compounds, termed "synthons", in the synthesis of stereospecific retinoid derivatives which are substituted with a dithiane ring of formula (II):

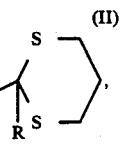
(II)

in which formula R has the same meaning as for formula (I), the dithiane ring being at the cis position when R is H and at the trans position when R is a thioalkyl radical. A preparation process which makes it possible to obtain, with a high stereospecificity, retinoids of formula (II) from synthons of formula (I) is described in the French Patent Application FR 91 07292 filed on Jun. 14, 1991 by the Applicant, the contents of this other application having to be considered as incorporated in the present application by reference.

The second subject of the present invention is a process for the preparation of the dithianepropenal of formula (Ia) where the dithiane group is at the cis position:

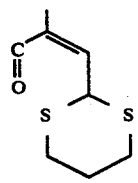
(Ia)

by reaction of ethyl β-formylmethacrylate of cis structure and of formula:

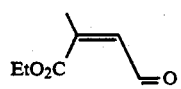
(III)

with Et=ethyl
with 1,3-propanedithiol in the presence of zinc triflate, so as to attach a dithiane ring to the formyl group at the cis position with elimination of water and to obtain the compound of formula:

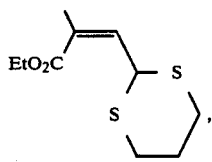
(IV)

by reduction of this compound (IV) in the presence of diisobutylaluminium hydride in order to obtain the dithianepropenol of formula:

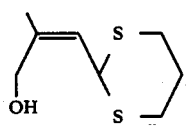
(V)

and by oxidation of the said propenol of formula (V) in order to obtain the cis-propenal of formula (Ia).

It has been found that the various reactions for the preparation of the cis-dithianepropenal of formula (Ia) are stereospecific and that from methyl β-formylmethacrylate of cis structure, a dithianepropenal is obtained which is also "cis", at least to a highly dominant degree.

The third subject of the present invention is a process for the preparation of a propenal of formula (I), where the dithiane ring is at the trans position, in which an alkylthiodithiane of formula:

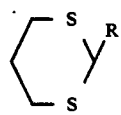

where R represents a $C_1$-$C_4$ thioalkyl radical, is reacted with n-butyllithium and then with ethoxymethacrolein of formula:

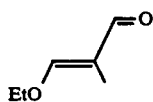

with Et=ethyl
and a hydrolysis is carried out, so as to obtain the compound of formula:

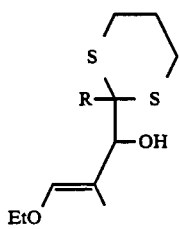

with Et=ethyl
which is subsequently treated with acetone and then with an acid in order to obtain the said compound of formula (I) where the dithiane group is at the trans position.

The examples given below, as purely illustrative and nonlimiting, will make it possible to understand the invention better.

EXAMPLE 1

Preparation of the Compound of Formula (Ia)

The reaction is carried out according to the following scheme:

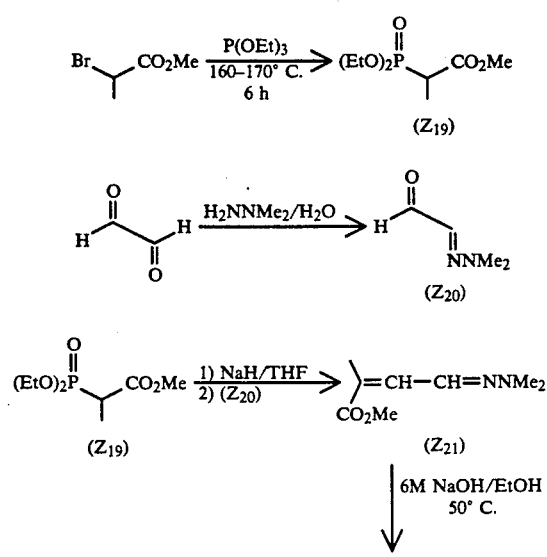

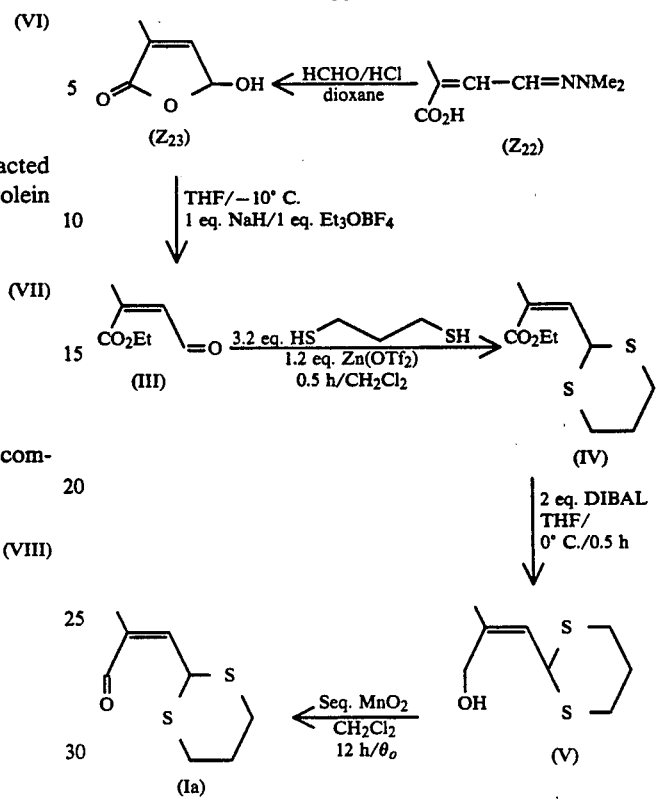

In this scheme, the intermediate compounds are indicated by the references ($Z_i$), i being an integer ranging from 19 to 23. $\theta_o$ is room temperature.

1st stage: Preparation of methyl diethylphosphonopropionate ($Z_{19}$) of formula:

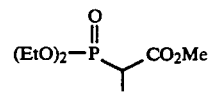

with
Me=methyl
Et=ethyl.

One equivalent of methyl 2-bromopropionate (22.5 ml - 0.2 mol) is mixed with 1.5 equivalents of triethyl phosphite (51.5 ml - 0.3 mol). The mixture is heated progressively to 160°-170° C. This temperature is maintained for 6 hours. In the course of the reaction, the ethyl bromide formed distils (boiling point=40° C.) as well as the methyl acrylate (boiling point=80° C.). The excess of reagent is then distilled under vacuum (60°-65° C., at 66 pascals). The phosphonopropionate is distilled (75°-80° C., at 66 pascals) in order to obtain 44.84 g of a colourless liquid.

The product obtained has the following characteristics:

a) Thin layer chromatography TLC (hexane/ethyl acetate: 70/30):
$R_f$=0.17.

b) Molecular mass M=224.2 g c) The structure was confirmed by nuclear magnetic resonance ($^1$H and $^{13}$C NMR) (200 MHz) (CDCl$_3$) and by study of the infrared (IR) spectrum (CCl$_4$).

2nd stage: Preparation of the mono-(N,N-dimethylhydrazone) of glyoxal ($Z_{20}$) of formula:

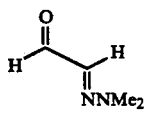

with Me=methyl.

1 equivalent of N,N-dimethylhydrazine (34.2 ml - 0.45 mol) is added dropwise and with stirring to 1.1 equivalents of glyoxal (0.5 mol - 29 ml of the reagent as a 30% aqueous solution) in water (300 ml). After 0.5 h at room temperature, the mixture is extracted with $CH_2Cl_2$ (3×150 ml). The combined organic phases are dried over $Na_2SO_4$ and then concentrated. The light yellow liquid (45 g) obtained is used as it is.

The product obtained has the following characteristics:
a) TLC (hexane/ethyl acetate: 70/30): $R_f \approx 0.23$.
b) M = 100.12 g
c) The structure was confirmed by NMR ($^1H$) (200 MHz) ($CDCl_3$) and by IR.

3rd stage: Preparation of methyl 4-(N,N-dimethylhydrazono)-2-methyl-2-butenoate ($Z_{21}$) of formula:

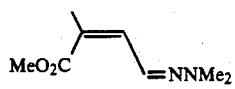

with Me=methyl.

Sodium hydride (1.07 g - 0.0446 mol) is suspended in anhydrous tetrahydrofuran (THF) (40 ml). The mixture is cooled to 0° C. and then 1 equivalent of the phosphonoacetate ($Z_{19}$) is added dropwise with stirring (10 g - 0.0446 mol). After 5 minutes, 1 equivalent of the hydrazone ($Z_{20}$) (4.46 g - 0.0446 mol) is added slowly to the mixture. A brown-yellow gum is quickly deposited at the bottom of the reaction flask. The reaction is monitored by thin layer chromatography until the starting materials have completely disappeared (15 to 30 minutes). The mixture is then hydrolysed by the addition of water (10 ml) and then extracted with ether (3×50 ml). The combined organic phases are washed with a saturated solution of NaCl (50 ml), dried over $Na_2SO_4$ and then concentrated. The residue is recrystallised in an acetone/pentane mixture; if it is too impure, flash chromatography is necessary (eluent=hexane/ethyl acetate: 80/20; silica treated with 3% of triethylamine). 7.21 g of white crystals are obtained.

The yield is: 95%

The characteristics of the product obtained are the following:
a) TLC (hexane/ethyl acetate: 70/30): $R_f \approx 0.56$.
b) M = 170.2 g
c) Melting point m.p. = 49°-50° C.
d) The structure was confirmed by NMR ($^1H$ and $^{13}C$) (200 MHz) ($CDCl_3$) and by IR.
e) Elemental analysis gives the following results:

| %   | Calculated | Found |
| --- | ---------- | ----- |
| C   | 56.46      | 56.28 |
| H   | 8.29       | 8.40  |
| N   | 16.46      | 16.40 |

4th stage: Preparation of 4-(N,N-dimethylhydrazono)-2-methyl-2-butenoic acid ($Z_{22}$) of formula:

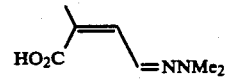

with Me=methyl.

The ester ($Z_{21}$) (10 g - 0.059 mol) is dissolved in a 1/1 mixture of ethanol and of 6M sodium hydroxide (800 ml). The reaction mixture is then stirred at 50° C. until the starting material has disappeared (30 min). It is then diluted by the addition of water (100 ml) and the bulk of the alcohol is evaporated under vacuum. The residue is first extracted with ether (2×100 ml) in order to remove all the organic degradation products. After a further addition of ether (200 ml) to the aqueous phase, the latter is acidified by the slow addition of concentrated sulphuric acid while monitoring the pH. As soon as pH of 3-4 is reached, the reaction mixture is extracted with ether (3×100 ml), dried over $Na_2SO_4$ and then concentrated. The residue is recrystallised in an acetone/pentane mixture. 8.75 g of product are obtained in the form of long, pale yellow needles.

The yield is: 95%

The characteristics of the product obtained are the following:
a) TLC (hexane/ethyl acetate: 70/30): $R_f \approx 0.07$.
b) M.p. = 145°-147° C.
c) M = 156.19 g
d) The structure was confirmed by NMR ($^1H$ and $^{13}C$) (200 MHz) ($CDCl_3$) and by IR.
e) Elemental analysis gives the following results:

| %   | Calculated | Found |
| --- | ---------- | ----- |
| C   | 53.83      | 54.00 |
| H   | 7.74       | 7.73  |
| N   | 17.94      | 18.19 |

5th stage: Preparation of 5-hydroxy-3-methyl-2(5H)-furanone ($Z_{23}$) of formula:

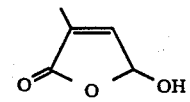

18 ml of 35% formaldehyde and 13 ml of concentrated hydrochloric acid are added to the hydrazone ($Z_{22}$) (6.5 g - 0.0416 mol) in solution in dioxane (130 ml). The mixture is stirred at room temperature until the starting material has disappeared (5 to 6 h). It is then poured onto crushed ice, extracted with methylene chloride (4×100 ml), dried over $Na_2SO_4$ and then concentrated.

The butenolide obtained is purified by flash chromatography (eluent=hexane/ethyl acetate/ether: 40/30/30). 3.75 g of beige crystals are obtained.

The yield is: 79%

The characteristics of the product obtained are the following:
a) TLC (hexane/ethyl acetate: 50/50): $R_f=0.29$.
b) M.p.=70°–72° C.
c) M=114.1 g
d) The structure was confirmed by NMR ($^1$H and $^{13}$C) (200 MHz) (CDCl$_3$) and by IR.
e) Elemental analysis gives the following results:

| % | Calculated | Found |
|---|---|---|
| C | 52.63 | 52.82 |
| H | 5.30 | 5.33 |

6th stage: Preparation of the compound of formula (III):

a) Preparation of triethyloxonium tetrafluoroborate (Et$_3$OBF$_4$).

To freshly distilled boron trifluoride etherate (30 ml - 0.243 mol) in solution in anhydrous ether (60 ml) under argon, there is added dropwise and with vigorous agitation 0.75 equivalent of epichlorohydrin (14.2 ml - 0.182 mol) such that there is spontaneous reflux. This reflux is maintained for 1 hour and then the mixture is left standing overnight. A translucent gel is deposited at the bottom of the reaction flask. It is filtered under argon, washed copiously with anhydrous ether and then dried using a vane pump. A white precipitate of 26 g of triethyloxonium tetrafluoroborate is obtained. It can be stored for several days in the refrigerator under argon.

The yield is: 78%
The molar weight is M=183.94 g b) Preparation of ethyl β-formylmethacrylate in the cis form of formula:

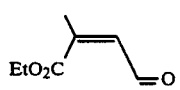

(III)

with Et=ethyl.

The butenolide (Z$_{23}$) (3 g - 0.026 mol) is solubilised in distilled methylene chloride (60 ml). After cooling the mixture to −10° C., 1 equivalent of sodium hydride (0.624 g - 0.026 mol) is added, followed immediately by 1 equivalent of triethyloxonium tetrafluoroborate (4.97 g - 0.026 mol). The mixture is stirred for 1.5 h from −10° C. to about 5° C., before being hydrolysed by the addition of one equivalent of triethylamine (3.6 ml - 0.026 mol) and of 30 ml of anhydrous ether. The pale yellow precipitate formed (complex of triethylamine and of boron trifluoride) is filtered and washed copiously with anhydrous ether. The residue is evaporated and then treated by chromatography on a silica column (eluent=hexane/ethyl acetate: 80/20; silica treated with 3% of triethylamine). 2.22 g of a yellow oil are obtained.

The yield is: 60%
The characteristics of the product are the following:
a) TLC (hexane/ethyl acetate: 70/30): $R_f=0.62$.
b) M=142.16 g
c) The structure was confirmed by NMR ($^1$H and $^{13}$C) (200 MHz) (CDCl$_3$) and by IR.
d) Elemental analysis gives the following results:

| % | Calculated | Found |
|---|---|---|
| C | 59.14 | 58.88 |
| H | 7.09 | 7.21 |

7th stage: Preparation of ethyl β-(1,3-dithiane)-methacrylate in the cis form of formula:

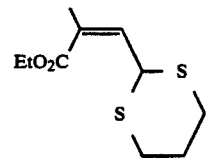

(IV)

with Et=ethyl.

a) Preparation of zinc triflate Zn(OTf)$_2$.

One equivalent of zinc carbonate (17.4 g - 0.139 mol) is dissolved in dry methanol (250 ml). Using a dropping funnel, 1.4 equivalents of triflic acid (50 g - 0.195 mol) are slowly added dropwise thereto. The reaction is exothermic and a vigorous evolution of CO$_2$ is observed. The mixture is stirred for 20 minutes at room temperature and then for 2 h at reflux. The methanol is then evaporated. The residue is dried by heating for 2.5 h at 130° C. under 330 pascals. 50.4 g of a white powder are obtained.

b) Preparation of the compound of formula (IV):

3.2 equivalents of 1,3-propanedithiol (4.85 ml - 0.048 mol) and 1.2 equivalents of Zn(OTf)$_2$ (6.54 g - 0.018 mol) are dissolved in distilled CH$_2$Cl$_2$ (80 ml) under argon. After stirring the mixture for 15 minutes at room temperature, 1 equivalent of the compound of formula (III) (2.2 g - 0.015 mol) in solution in CH$_2$Cl$_2$ (20 ml) is rapidly added dropwise. The reaction is complete after 0.5 h and the mixture is diluted by the addition of water (90 ml) and then of a saturated solution of NH$_4$Cl until a pH equal to 4–5 is reached (approximately 200 ml). The aqueous phase is extracted with a hexane/ether (1/1) mixture (4×100 ml). The combined organic phases are washed with a saturated solution of NH$_4$Cl (100 ml) in order to "break" the emulsion which is formed, then with 0.5M sodium hydroxide (3×100 ml), with a saturated solution of NaHCO$_3$ (100 ml), with water (2×100 ml) and finally with a saturated solution of NaCl (100 ml). After drying over Na$_2$SO$_4$ and evaporating the solvent, 3.6 g of a colourless oil are isolated.

The characteristics of the product obtained are the following:
a) TLC (hexane/ethyl acetate: 90/10): $R_f=0.36$.
b) M=232.37 g.
c) The structure was confirmed by NMR ($^1$H and $^{13}$C) (200 MHz) (CDCl$_3$) and by IR.
e) Elemental analysis gives the following results:

| % | Calculated | Found |
|---|---|---|
| C | 51.69 | 51.83 |
| H | 6.94 | 6.85 |

8th stage: Preparation of the compound (Z)-3-(1,3-dithian-2-yl)-2-methylpropenol of formula:

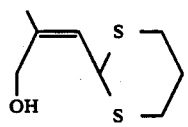
(V)

The ester of formula (IV) (3.5 g - 0.015 mol) is dissolved in anhydrous tetrahydrofuran (THF) (70 ml) under argon. After cooling the mixture to 0° C., 2.2 equivalents of diisobutylaluminium hydride (DIBAL) (33 ml of 1M solution in toluene) are rapidly added dropwise. After 0.5 h the reaction is complete and the mixture is hydrolysed by the slow addition of methanol (1.55 ml). The whole is poured into a mixture of ethyl acetate (600 ml) and of a saturated solution of sodium tartrate (74 ml). A vigorous stirring of this mixture for 1 h makes it possible to "break" the gel which is formed. The aqueous phase is then extracted with ethyl acetate (3×100 ml). The combined organic phases are washed with a saturated solution of NaCl (100 ml), dried over Na$_2$SO$_4$ and then concentrated. The residue is treated by chromatography on a silica column (eluent=hexane/ethyl acetate: 80/20; silica treated with 3% of triethylamine) to give 2.30 g of a colourless oil.

The yield is: 81%

The product obtained has the following characteristics:
a) TLC (hexane/ethyl acetate: 70/30):
R$_f$=0.23.
b) The structure was confirmed by NMR ($^1$H and $^{13}$C) (200 MHz) (CDCl$_3$) and by IR.
e) Elemental analysis gives the following results:

| %  | Calculated | Found |
|----|-----------|-------|
| C  | 50.49     | 50.69 |
| H  | 7.41      | 7.69  |

9th stage: Preparation of (Z)-3-(1,3-dithian-2-yl)-2-methylpropenal of formula:

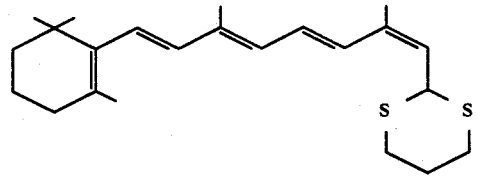
(Ia)

The alcohol of formula (V) (2.3 g - 0.012 mol) is dissolved in distilled CH$_2$Cl$_2$ (150 ml) under argon. Approximately 5 equivalents of manganese dioxide (5.25 g) are added to the mixture with vigorous stirring. After 4 h at room temperature, the suspension is filtered on a thin layer of silica. The silica is washed copiously with ethyl acetate. The filtrate is concentrated under vacuum. 2.15 g of beige crystals are obtained.

The yield is: 95%

The characteristics of the product are the following:
a) TLC (hexane/ethyl acetate: 70/30):
R$_f$=0.52.
b) M.p.=102° C.
c) M=188.32 g
d) The structure was confirmed by NMR ($^1$H and $^{13}$C) (200 MHz) (CDCl$_3$) and by IR.
e) Elemental analysis gives the following results:

| %  | Calculated | Found |
|----|-----------|-------|
| C  | 51.02     | 51.20 |
| H  | 6.42      | 6.47  |

EXAMPLE 2

Use of the compound of formula (Ia) for the synthesis of a retinoid (Z$_{30}$) of formula:

The preparation is carried out according to the following reaction scheme:

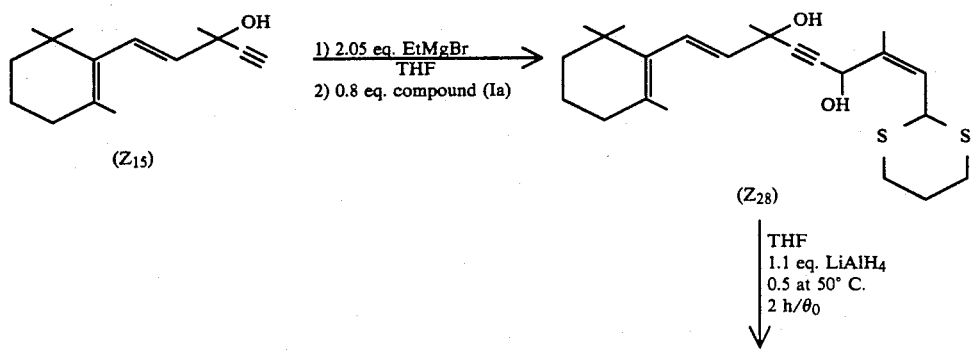

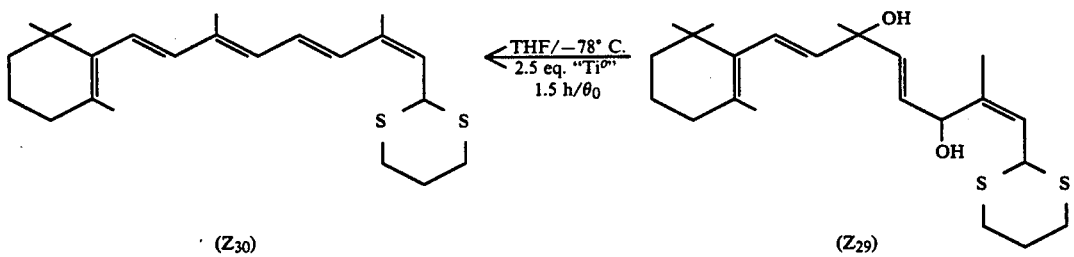

(Z<sub>30</sub>)    (Z<sub>29</sub>)

In this scheme, the intermediate compounds are indicated by the reference ($Z_i$), i being an integer ranging from 28 to 30. $\theta_0$ denotes room temperature.

1st stage: Preparation of the compound ($Z_{28}$):

a) Preparation of the ethynyl-β-ionol ($Z_{15}$) of formula:

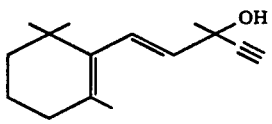

Dry magnesium (5.1 g - 0.210 mol) and anhydrous tetrahydrofuran (THF) (100 ml) are placed in a 250 cm³, three-necked flask, equipped with a dropping funnel and a reflux condenser. A solution of ethyl bromide (15.7 ml - 0.210 mol) in anhydrous THF (30 ml) is then slowly added under argon. After reaction of the magnesium, the mixture is held for 1 hour at room temperature.

In addition, a 500 cm³, three-necked flask is equipped with a reflux condenser connected to an oil burner, with a dropping funnel and with a gas diffuser for acetylene (acetylene passes first through a trap at −78° C.). The acetylene is then dissolved for 1 h in anhydrous THF (200 ml) at between −30° and −20° C. After removing the cooling bath, the magnesium derivative is rapidly added dropwise, the stream of acetylene still being maintained. The temperature is held below 35° C.

After addition of the magnesium derivative, the mixture is stirred for 30 minutes at room temperature. β-Ionone (21.2 ml - 0.104 mol) in solution in anhydrous THF (20 ml) is then added dropwise over 30 minutes. With the stream of acetylene still maintained, the reaction is complete at the end of one hour and the green-yellow solution obtained is poured slowly into a saturated solution of NH<sub>4</sub>Cl (250 ml). The mixture is extracted with ether (3×50 ml), washed with water (50 ml), then with a saturated solution of NaCl (100 ml), dried over Na<sub>2</sub>SO<sub>4</sub> and finally concentrated. The residue is distilled (125° C./395 pascals) in order to obtain a colourless oil. 18.16 g of product are obtained. The compound is stored in a freezer and protected from light.

The yield is: 80%

The characteristics of the product obtained are the following:

a) TLC (hexane/ethyl acetate: 70/30): R<sub>f</sub>≃0.64.

b) M=218.34 g c) M.p.=21° C.

d) The structure was confirmed by NMR (¹H and ¹³C) (200 MHz) (CDCl<sub>3</sub>) and by IR.

b) Preparation of the compound ($Z_{28}$) of formula:

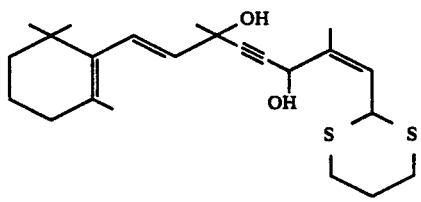

In a first step, a Grignard reagent is prepared from 2.05 equivalents of magnesium (79.2 mg - 3.26 mmol) in anhydrous tetrahydrofuran (THF) (10 ml) and under argon. 2.1 equivalents of bromoethane (0.25 ml - 3.34 mmol) in solution in anhydrous THF (10 ml) are added dropwise. As soon as the magnesium is dissolved, 1 equivalent of the compound ($Z_{15}$) (348 mg - 1.59 mmol) in solution in THF (10 ml) is slowly added. Ethane is observed to be evolved. After 2 h of reaction at room temperature, 0.8 equivalent of the synthon Ia (0.24 g - 1.275 mmol) in solution in THF (10 ml) is rapidly added to the mixture. After 1.5 h, the content of compound ($Z_{28}$) no longer developing as noted by thin layer chromatography, the mixture is hydrolysed by the slow addition of a saturated solution of NH<sub>4</sub>Cl (20 ml; pH=7) and then of water (10 ml). The aqueous phase is extracted with ether (3×50 ml). The combined organic phases are washed with a saturated solution of NaCl (80 ml), dried over Na<sub>2</sub>SO<sub>4</sub> and then concentrated. The residue is purified by flash chromatography (eluent-=hexane/ethyl acetate: 80/20). 430 mg of a very "foamy", yellow oil are obtained, which can be stored for several months in a freezer, but it degrades very quickly at room temperature.

The yield is: 83% in relation to the synthon Ia.

The characteristics of the product obtained are the following:

a) TLC (hexane/ethyl acetate: 70/30): R<sub>f</sub>≃0.24.

b) M=406.66 g c) The structure was confirmed by NMR (¹H) (200 MHz) (CDCl<sub>3</sub>) and by IR.

2nd stage: Preparation of the compound ($Z_{29}$) of formula:

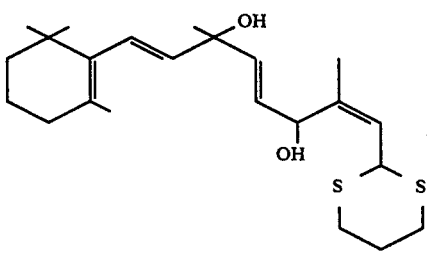

1.4 equivalents of LiAlH₄ (1.1 ml of 0.89M solution in ether) are added dropwise to 1 equivalent of the compound (Z$_{28}$) (350 mg - 0.86 mmol) in solution in anhydrous tetrahydrofuran (THF) (35 ml) under argon. When the addition is complete, the reaction flask equipped with a reflux condenser is immersed in a bath previously heated to 50° C. At this temperature, the yellow mixture slowly darkens. After 1.5 h, since the mixture is becoming excessively degraded, the temperature is lowered and stirring is continued at room temperature for 2 h. The mixture is then carefully hydrolysed by the addition of a saturated solution of NH₄Cl (20 ml; pH=7) and then of water (10 ml). The aqueous phase is extracted with ether (3×20 ml). The combined organic phases are washed with a saturated solution of NaCl (50 ml), dried over Na₂SO₄ and then concentrated. The residue is purified by flash chromatography (eluent=hexane/ethyl acetate: 90/10). 105 mg of a yellow oil are obtained; this oil can be stored with difficulty in the freezer and degrades very quickly at room temperature.

The yield is: 55%

The product obtained has the following characteristics:

a) TLC (hexane/ethyl acetate: 70/30): R$_f$≈0.23.

b) M=408.67 g c) The structure was confirmed by NMR (¹H) (200 MHz) (CDCl₃) and by IR.

3rd stage: Preparation of the retinoid (Z$_{30}$) of formula:

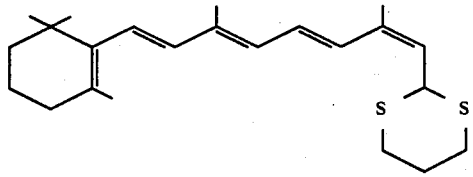

In order to prepare the reagent containing low valency titanium (Ti°), titanium trichloride (1.5 g - 9.72 mmol) is weighed in a dry flask equipped with a reflux condenser; the flask is purged with argon and anhydrous tetrahydrofuran (THF) (48 ml) is added, followed by 0.5 equivalent of LiAlH₄ (2.2 ml of 2.2M solution in ether). The mixture is stirred for 10 minutes at room temperature, then 0.42 equivalent of triethylamine (0.57 ml - 4.08 mmol) are added and the whole is heated at reflux for 1.5 h.

Protected from light, 2.1 equivalents of the reagent obtained (3.7 ml of the suspension) are added, dropwise and at −78° C., to 1 equivalent of compound Z$_{29}$ (0.14 g - 0.343 mmol), in solution in anhydrous THF (20 ml). The mixture is then immersed in a bath at 50° C. and stirred for 0.5 h at this temperature, then slowly hydrolysed at −30° C. by addition of water (10 ml). The aqueous phase is extracted with ether (4×15 ml). The combined organic phases are filtered on a thin layer of Celite, dried over Na₂SO₄ and then concentrated under vacuum at room temperature. The residue obtained is purified by flash chromatography (eluent=hexane/ether: 95/5). 64 mg of yellow crystals are obtained.

The yield is: 35%

The product obtained has the following characteristics:

a) TLC (hexane/ethyl acetate: 70/30): R$_f$≈0.80.

b) M=374.66 g c) The structure was confirmed by NMR (¹H) (200 MHz) (CDCl₃).

EXAMPLE 3

Preparation of the compound of formula (Ib)

The preparation is carried out according to the scheme below.

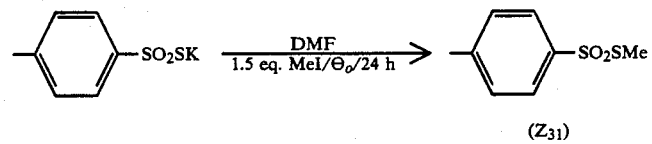

(Z$_{31}$)

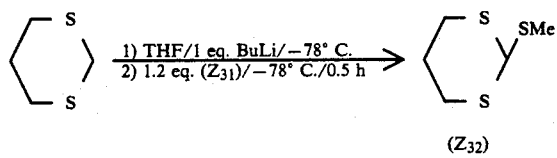

(Z$_{32}$)

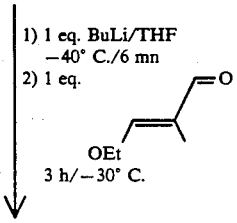

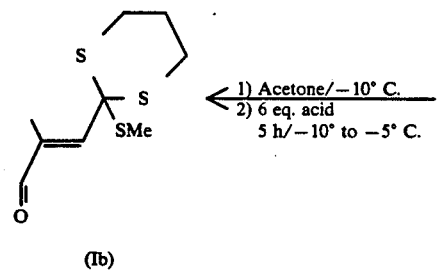
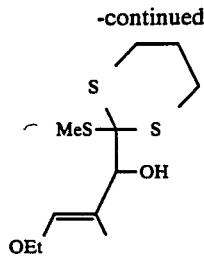

(Ib)    (Z$_{33}$)

In this scheme, the intermediate compounds are indicated by the references (Z$_i$), i being an integer ranging from 31 to 33; θ$_0$ denotes room temperature.

1st stage: Preparation of S-methyl 4-methylbenzenethiosulphonate (Z$_{31}$) of formula:

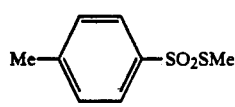

with Me=methyl.

1.3 equivalent of iodomethane (12.8 ml - 0.201 mol) are rapidly added dropwise to 1 equivalent of potassium tolylthiosulphonate (35 g - 0.155 mol) in solution in dimethylformamide distilled over a 4 angströma molecular sieve (500 ml). The mixture is stirred for 24 h at room temperature. In the course of reaction, it slowly turns brown. After diluting by the addition of water (450 ml), the mixture is extracted with CH$_2$Cl$_2$ (5×150 ml). The combined organic phases are washed with a saturated solution of NaHCO$_3$ (2×150 ml) and with a saturated solution of Na$_2$SO$_3$ (200 ml), which enables the mixture to be decolorised, and then washed copiously with water (5×200 ml). After a final wash with a saturated solution of NaCl (250 ml) followed by drying over Na$_2$SO$_4$ and concentrating, a yellow precipitate is obtained. It is recrystallised in ether containing a small amount of pentane. 27.91 g of large white crystals are obtained.

The yield is: 89%

The characteristics of the product obtained are the following:

a) TLC (hexane/ethyl acetate: 70/30):
R$_f$≈0.5.

b) M.p.=58°-59° C.

c) The structure was confirmed by NMR ($^1$H and $^{13}$C) (200 MHz) (CDCl$_3$) and by IR.

2nd stage: Preparation of 2-methylthio-1,3-dithiane (Z$_{32}$) of formula:

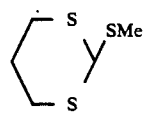

with Me=methyl.

A solution of 1,3-dithiane (6 g - 0.05 mol) in anhydrous tetrahydrofuran (THF) (200 ml) is cooled to −78° C.; 1 equivalent of n-butyllithium (33.3 ml of 1.5M solution) is rapidly added dropwise. The mixture is stirred for 2 h at this temperature; it is then added using a cannula to 1.2 equivalents of compound (Z$_{31}$) (12.14 g - 0.06 mol) in solution in anhydrous THF (80 ml) at −78° C. During the addition (which takes place over approximately 35 minutes), a white precipitate is progressively formed. Stirring is maintained at −78° C. for 0.5 h and then the mixture is hydrolysed by the addition of 0.05 N HCl (600 ml). The THF is evaporated and the residue is then extracted with a CH$_2$Cl$_2$/pentane (1/1) (4×200 ml) mixture. The combined organic phases are washed with a saturated solution of NaHCO$_3$ (3×100 ml), with a saturated solution of NaCl (250 ml), then dried over Na$_2$SO$_4$ and concentrated. The residue is quickly subjected to chromatography on a silica column (eluent=hexane/ether: 95/5) in order to remove the excess methyl tolylthiosulphonate (Z$_{31}$) 7.90 g of a colourless oil are obtained, which precipitates in the freezer.

The yield is: 95%

The characteristics of the product obtained are the following:

a) TLC (hexane/ether: 90/10):
R$_f$≈0.54.

b) M=166.33 g c) The structure was confirmed by NMR ($^1$H and $^{13}$C) (200 MHz) (CDCl$_3$).

3rd stage: Preparation of ethyl 3-(2-methylthio-1,3-dithian-2-yl)-3-hydroxy-2-methyl-1-propenyl ether (Z$_{33}$) of formula:

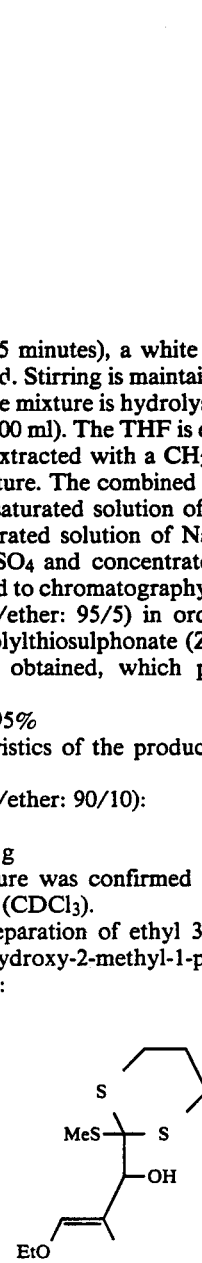

with
Me=methyl
Et=ethyl.

1 equivalent of n-butyllithium (30 ml of 1.5M solution) is rapidly added dropwise to the ortho thioester (Z$_{32}$) (7.5 g - 0.045 mol) in solution in distilled tetrahydrofuran (THF) (150 ml) at −40° C. After 6 minutes of reaction at this temperature, 1 equivalent of ethoxymethacrolein (5.35 ml - 0.045 mol) is added. Stirring is maintained for 3 h at −30° C. and then the mixture is hydrolysed by the addition of a saturated solution of NH$_4$Cl (approximately 200 ml - pH=5). As soon as the temperature has risen to room temperature, the mixture is extracted with ether (3×200 ml). The combined organic phases are washed with a saturated solution of NaHCO$_3$ (2×200 ml), water (200 ml), a saturated solution of NaCl (200 ml), then dried over Na$_2$SO$_4$ and concentrated. The yellow residue is purified by flash chromatography (eluent=hexane/ether: 90/10). 10.25 g of a pale yellow oil are obtained which is stored in the freezer where it precipitates.

The yield is: 81%

The product obtained has the following characteristics:
a) TLC (hexane/ether: 90/10):
$R_f \approx 0.12$.
b) M.p.=39°–40° C.
c) M=280.48 g
d) The structure was confirmed by NMR ($^1$H and $^{13}$C) (200 MHz) (CDCl$_3$) and by IR.
e) Elemental analysis gives the following results:

| % | Calculated | Found |
|---|---|---|
| C | 47.11 | 47.37 |
| H | 7.19 | 7.22 |

4th stage: Preparation of the compound (E)-3-(2-methylthio-1,3-dithian-2-yl)-2-methylpropenal of formula (Ib)

with Me=methyl.

The enol ether ($Z_{33}$) (9 g - 0.032 mol) is dissolved in acetone (300 ml) at −10° C.; 6 equivalents of acid (54 ml of 10% aqueous sulphuric acid) are slowly added to the mixture. The latter is stirred for 5 h between −10° and −5° C. before being hydrolysed by the addition of a saturated solution of NaHCO$_3$ (approximately 200 ml; pH=5) and water (200 ml). The acetone is evaporated and then the mixture is extracted with ether (5×100 ml).

The combined organic phases are washed with a saturated solution of NaHCO$_3$ (70 ml; pH=7) and a saturated solution of NaCl (250 ml). After drying over Na$_2$SO$_4$ and concentrating, the residue is purified by flash chromatography (eluent=hexane/ether: 90/10). 5.62 g of a yellow oil are obtained.

The yield is: 75%

The characteristics of the product obtained are the following:
a) TLC (hexane/ether: 90/10):
$R_f \approx 0.28$.
b) M=234.41 g
c) The structure was confirmed by NMR ($^1$H and $^{13}$C) (200 MHz) (CDCl$_3$) and by IR.
e) Elemental analysis gives the following results:

| % | Calculated | Found |
|---|---|---|
| C | 46.12 | 46.22 |
| H | 6.02 | 5.95 |

EXAMPLE 4

Use of the compound of formula (Ib) for the synthesis of the retinoid of formula:

with Me=methyl.

The preparation is carried out according to the scheme given below:

In this scheme, the intermediate compounds are indicated by the references ($Z_i$), i being an integer equal to 35 or 36.

The acetylenic compound ($Z_{15}$) is prepared as described in Example 2.

1st stage: Preparation of the compound ($Z_{35}$) of formula:

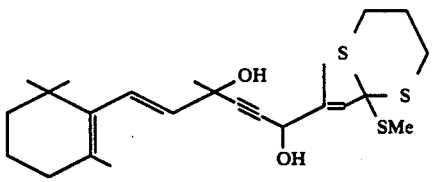

with Me=methyl.

In a first step, a Grignard reagent is prepared from 2.05 equivalents of magnesium (1.13 g - 0.047 mol) in anhydrous tetrahydrofuran (THF) (20 ml) and under argon. 2.1 equivalents of bromoethane (3.6 - 0.048 mol) in solution in anhydrous THF (20 ml) are added dropwise. As soon as all the magnesium is dissolved, 1 equivalent of the compound ($Z_{15}$) (5 g - 0.0229 mol) in solution in THF (50 ml) is slowly added. Ethane is observed to be evolved. After 1.5 h of reaction at room temperature, 1 equivalent of the compound of formula (Ib) (5.37 g - 0.0229 mol) in solution in THF (50 ml) is rapidly added to the mixture. After 1 h, the content of compound ($Z_{35}$) no longer developing, as noted by thin layer chromatography, the mixture is hydrolysed by the slow addition of a saturated solution of $NH_4Cl$ (50 ml), followed by water (50 ml). The aqueous phase is extracted with ether (3×80 ml). The combined organic phases are washed with a saturated solution of NaCl (100 ml), dried over $Na_2SO_4$ and then concentrated. The residue is purified by flash chromatography (eluent=hexane/ethyl acetate: 85/15). 9.33 g of a very "foamy", yellow oil are obtained.

The yield is: 90%

The product obtained has the following characteristics:

a) TLC (hexane/ethyl acetate: 70/30):
$R_f$=0.29.

b) M=452.75 g c) The structure was confirmed by NMR ($^1H$) (200 MHz) ($CDCl_3$) and by IR.

2nd stage: Preparation of the diol ($Z_{36}$) of formula:

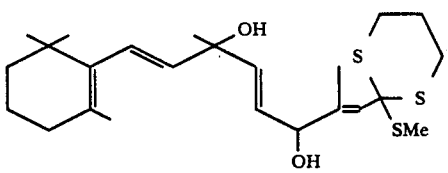

with Me=methyl.

1.1 equivalents of $LiAlH_4$ (2.7 ml of 1M solution in ether) are added dropwise to 1 equivalent of the compound ($Z_{35}$) (1.1 g - 2.43 mmol) in solution in anhydrous tetrahydrofuran (THF) (140 ml) under argon. When the addition is complete, the flask equipped with a reflux condenser is immersed in a bath heated beforehand to 55° C. At this temperature, the yellow mixture slowly takes on a violet colour. After 0.5 h, the reaction is complete and the mixture is carefully hydrolysed by the addition of a saturated solution of $NH_4Cl$ (60 ml), followed by water (20 ml). The aqueous phase is extracted with ether (3×70 ml). The combined organic phases are washed with a saturated solution of NaCl (100 ml), dried over $Na_2SO_4$ and then concentrated. The residue is purified by flash chromatography (eluent=hex-ane/ethyl acetate: 90/10). 0.9 g of a yellow oil is obtained.

The yield is: 81%

The characteristics of the product obtained are the following:

a) TLC (hexane/ethyl acetate: 70/30):
$R_f$=0.21.

b) M=454.7 g c) The structure was confirmed by NMR ($^1H$) (200 MHz) ($CDCl_3$).

3rd stage: Preparation of the retinoid of formula:

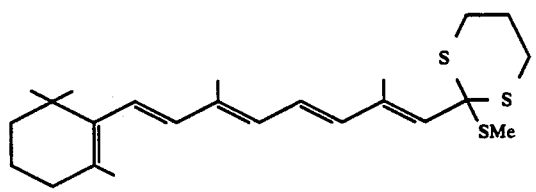

with Me=methyl.

In order to prepare the reagent containing low valency titanium (Ti°), titanium trichloride (0.5 g - 3.24 mmol) is weighed into a dry flask equipped with a reflux condenser. The assembly is purged with argon and anhydrous tetrahydrofuran (THF) (80 ml) is added. 0.5 equivalent of $LiAlH_4$ (1.47 ml of 1.1M solution in ether) is then added. The mixture is stirred for 10 minutes at room temperature, then 0.2 equivalent of triethylamine (0.09 ml - 0.648 mmol) is added and the whole is heated at reflux for 1.5 h.

Protected from light, 2 equivalents of the reagent containing the titanium (66.4 ml of the suspension) are added, dropwise and at 50° C., to 1 equivalent of compound ($Z_{36}$) (0.6 g - 1.32 mmol) in solution in anhydrous THF (30 ml). The mixture is stirred for 0.5 h at this temperature and then it is slowly hydrolysed at −30° C. by the addition of water (90 ml). The aqueous phase is extracted with ether (4×80 ml). The combined organic phases are filtered on a thin layer of Celite, dried over $Na_2SO_4$ and then concentrated under vacuum at room temperature. The residue obtained is purified by flash chromatography (eluent=hexane/ether: 95/5). 0.82 g of a yellow oil is obtained.

The yield is: 60%.

The product obtained has the following characteristics:

a) TLC (hexane/ethyl acetate: 70/30):
$R_f$=0.86.

b) M=420.76 g c) The structure was confirmed by NMR ($^1H$) (200 MHz) ($CDCl_3$) and by IR.

We claim:

1. Propenals of formula:

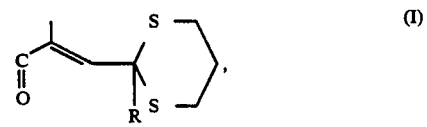

in which formula R is hydrogen or a $C_1$-$C_4$ thioalkyl radical, the dithiane ring being at the cis position with respect to the aldehyde function when R is H, and at the trans position when R is a thioalkyl radical.

2. Propenal according to claim 1, of cis structure and of formula:

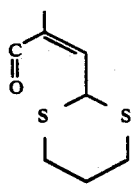
(Ia)

3. Propenal according to claim 1, of trans structure and of formula:

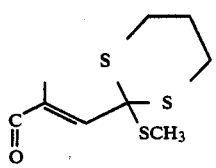
(Ib)

4. Process for the preparation of the propenal according to claim 2, characterised in that ethyl β-formylmethacrylate of cis structure and of formula:

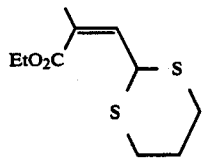
(III)

in which formula Et is an ethyl group, is reacted with 1,3-propanedithiol in the presence of zinc triflate so as to obtain the compound of formula:

(IV)

where Et has the same meaning as indicated above, in that this compound of formula (IV) is reduced in the presence of diisobutylaluminium hydride in order to obtain the dithianepropenol of formula:

(V)

and in that the said compound of formula (V) is oxidised in order to obtain the cis-propenal of formula (Ia).

* * * * *